(12) United States Patent
Bacon et al.

(10) Patent No.: US 9,008,339 B1
(45) Date of Patent: *Apr. 14, 2015

(54) DELIVERING FUNDAMENTAL FREQUENCY AND AMPLITUDE ENVELOPE CUES TO ENHANCE SPEECH UNDERSTANDING

(75) Inventors: Sid P. Bacon, Phoenix, AZ (US); Christopher A. Brown, Tempe, AZ (US); Frederic Apoux, Columbia, SC (US)

(73) Assignee: Arizona Board of Regents for and on behalf of Arizona State University, Scottsdale, AZ (US)

( * ) Notice: Subject to any disclaimer, the term of this patent is extended or adjusted under 35 U.S.C. 154(b) by 270 days.

This patent is subject to a terminal disclaimer.

(21) Appl. No.: 13/594,418

(22) Filed: Aug. 24, 2012

Related U.S. Application Data

(63) Continuation of application No. 12/433,851, filed on Apr. 30, 2009, now Pat. No. 8,280,087.

(60) Provisional application No. 61/049,349, filed on Apr. 30, 2008.

(51) Int. Cl.
*H04R 25/00* (2006.01)

(52) U.S. Cl.
CPC .................................. *H04R 25/353* (2013.01)

(58) Field of Classification Search
CPC .... H04R 25/70; H04R 25/356; H04R 25/505; H04R 25/554; H04R 25/353; H04R 25/453; H04R 25/502; H04R 2225/43; H04R 2430/03
USPC .................. 381/312, 316, 320, 321; 704/270
See application file for complete search history.

(56) References Cited

U.S. PATENT DOCUMENTS

| | | |
|---|---|---|
| 2002/0012438 A1* | 1/2002 | Leysieffer et al. ............ 381/312 |
| 2005/0245991 A1 | 11/2005 | Faltys et al. |
| 2005/0261748 A1 | 11/2005 | Van Dijk |
| 2006/0080087 A1* | 4/2006 | Vandali et al. ................ 704/207 |
| 2007/0135862 A1 | 6/2007 | Nicolai et al. |
| 2007/0217482 A1* | 9/2007 | Pelissier et al. ............... 375/130 |

FOREIGN PATENT DOCUMENTS

WO    WO 92/08330    5/1992

OTHER PUBLICATIONS

Assmann, P.F. (1999). "Fundamental frequency and the intelligibility of competing voices," Proc. 14th Int. Cong. of Phonetic Sci. , 179-182.

Assmann, P.F. and Summerfield, Q. (1990). "Modeling the perception of concurrent vowels: vowels with different fundamental frequencies," J. Acoust. Soc. Am. 88, 680-697.

(Continued)

*Primary Examiner* — Brian Ensey
(74) *Attorney, Agent, or Firm* — Fish & Richardson P.C.

(57) ABSTRACT

Systems, apparatus, and techniques are described to perform operations including receiving speech that includes audio signals from a talker. A fundamental frequency, unique to the talker, is extracted from the audio signals. A tone in frequency with the extracted fundamental frequency of the received speech is modulated and the modulated tone is delivered to an audio transducing device.

21 Claims, 7 Drawing Sheets

(56) References Cited

OTHER PUBLICATIONS

Bacon, S.P., Opie, J.M. and Montoya, D.Y. (1998). "The effects of hearing loss and noise masking on the masking release for speech in temporally complex backgrounds," J Speech Lang Hear Res 41, 549-563.

Berenstein, C.K., Mens, L.H.M., Mulder, J.J.S. and Vanpoucke, F.J. (2008). "Current steering and current focusing in cochlear implants: comparison of monopolar, tripolar, and virtual channel electrode configurations," Ear Hear 29, 250-260.

Binns, C. and Culling, J.F. (2007). "The role of fundamental frequency contours in the perception of speech against interfering speech," J. Acoust. Soc. Am. 122, 1765.

Bird, J. and Darwin, C.J. (1997). "Effects of a difference in fundamental frequency in separating two sentences," Paper for the 11th Int. Conf. on Hear., 7 pages.

Blarney, P.J., Dowell, R.C., Brown, A.M., Clark, G.M. and Seligman, P.M. (1987). "Vowel and consonant recognition of cochlear implant patients using formant-estimating speech processors," J. Acoust. Soc. Am. 82, 48-57.

Blarney, P.J., Dowell, R.C., Tong, Y.C., Brown, A.M., Luscombe, S.M. and Clark, G.M. (1984). "Speech processing studies using an acoustic model of a multiple-channel cochlear implant," J. Acoust. Soc. Am. 76, 104-110.

Brokx, J. and Nooteboom, S. (1982). "Intonation and the perceptual separation of simultaneous voices," J. Phonetics 10, 23-36.

Brown, C.A. and S. P. Bacon, "Low frequency speech cues and simulated electric-acoustic hearing," J. Acoust. Soc. Am. 125(3): .1658-1665 (Mar. 2009).

Brown, C.A. and S. P. Brown, "The effect of fundamental frequency in simulated electric-acoustic hearing," Acoust. Soc. Am., Salt Lake City, May 2007(Poster, 1 page).

Brown, C.A. and S. P. Brown, "The effect of fundamental frequency in simulated electric-acoustic hearing," J. Acoust. Soc. Am., vol. 121, No. 5, Pt. 2, p. 3093, Abstract No. 2pPP8 (May 2007).

Brown, C.A. and S.P. Bacon, "A new approach to electric-acoustic stimulation," Acoust. Soc. Am, Jul. 2008, Paris, France, (17 slides).

Brown, C.A. and S.P. Bacon, "A new approach to electric-acoustic stimulation," J. Acoust. Soc. Am. , vol. 123, No. 5, Pt. 2, May 2008, p. 3054.

Brown, C.A. and S.P. Bacon, "Achieving electric-acoustic benefit with a modulated tone," Ear and Hearing, vol. 30, No. 5, pp. 489-493, Oct. 2009.

Brown, C.A. and S.P. Bacon, "Learning effects in simulated electric-acoustic hearing," Thirty-First Annual Mid Winter Research Meeting of the Association for Research in Otolaryngology, Phoenix, AZ, Mar. 2008, (Poster, 1 page).

Brown, C.A. and S.P. Bacon, "Learning effects in simulated electric-acoustic hearing," Abstracts of the Thirty-First Annual Mid Winter Research Meeting of the Association for Research in Otolaryngology (ARO Abstracts), vol. 21, p. 279, Abstract No. 818, Feb. 16-21, Phoenix, AZ, Mar. 2008.

Brown, C.A., "The role of fine structure cues in enhancing speech reception for cochlear implant users," Cochlear Corp., Apr. 2009, (35 slides).

Carhart, R. and Tillman, T.W. (1970). "Interaction of competing speech signals with hearing losses," Arch Otolaryngol 91, 273-279.

Carhart, R., Tillman, T.W. and Greetis, E.S. (1969). "Perceptual masking in multiple sound backgrounds," J Acoust Soc Am 45, 694-703.

Chang et al., "Unintelligible low-frequency sound enhances simulated cochlear-implant speech recognition in noise," IEEE Trans. Biomed. Eng. vol. 53, No. 12, pp. 2598-2601 (Dec. 2006).

Chatterjee, M. and Peng, S. (2008). "Processing F0 with cochlear implants: Modulation frequency discrimination and speech intonation recognition," Hear Res 235, 143-156.

Culling, J.F. and Darwin, C.J. (1993b). "Perceptual separation of simultaneous vowels: within and across-formant grouping by F0," J. Acoust. Soc. Am. 93, 3454-3467.

Cullington, H.E. and Zeng, F. (2008). "Speech recognition with varying numbers and types of competing talkers by normal-hearing, cochlear-implant, and implant simulation subjects," J. Acoust. Soc. Am. 123, 450-461.

Dorman, M.F. and Loizou, P.C. (1998). "The identification of consonants and vowels by cochlear implant patients using a 6-channel continuous interleaved sampling processor and by normal-hearing subjects using simulations of processors with two to nine channels," Ear Hear. 19, 162-166.

Dorman, M.F. and P.C. Loizou (1997), Speech Intelligibility as a Function of the Number of Channels of Stimulation for Normal-Hearing Listeners and Patients with Cochlear Implants, The American Journal of Oncology, 18: S113-S114.

Dorman, M.F. et al. (1997), "Simulating the effect of cochlear-implant electrode insertion depth on speech understanding," J. Acoust. Soc. Am. 102(5), Pt. 1 pp. 2993-2996.

Dorman, M.F. et al. (1998), "The identification of speech in noise by cochlear implant patients and normal-hearing listeners using 6-chanel signal processors," Ear & Hearing 19(6): 481-484.

Dorman, M.F. et al. (1998), "The recognition of sentences in noise by normal-hearing listeners using simulations of cochlear-implant signal processors with 6-20 channels," J. Acoust. Soc. Am. 104(6): 3583-3585.

Dorman, M.F., Loizou, P.C. and Rainey, D. (1997). "Speech intelligibility as a function of the number of channels of stimulation for signal processors using sine-wave and noise-band outputs," J. Acoust. Soc. Am. 102, 2403-2411.

Dorman, M.F., Spahr, A.J., Loizou, P.C., Dana, C.J. and Schmidt, J.S. (2005). "Acoustic simulations of combined electric and acoustic hearing (EAS)," Ear Hear. 26, 371-380.

Duquesnoy, A.J. (1983). "Effect of a single interfering noise or speech source upon the binaural sentence intelligibility of aged persons," J Acoust Soc Am 74, 739-743.

Faulkner et al., "Speech pattern hearing aids for the profoundly hearing impaired: Speech perception and auditory abilities", J. Acoust. Soc. Am. 91 (4), Pt. 1, Apr. 1992, pp. 2136-2155.

Faulkner, A. and Rosen, S. (1999). "Contributions of temporal encodings of voicing, voicelessness, fundamental frequency, and amplitude variation to audio-visual and auditory speech perception," J. Acoust. Soc. Am. 106, 2063-2073.

Faulkner, A., Ball, V., Rosen, S., Moore, B.C. and Fourcin, A. (1992). "Speech pattern hearing aids for the profoundly hearing impaired: speech perception and auditory abilities," J. Acoust. Soc. Am. 91, 2136-2155.

Festen, J.M. and Plomp, R. (1983). "Relations between auditory functions in impaired hearing," J Acoust Soc Am 73, 652-662.

Festen, J.M. and Plomp, R. (1990). "Effects of fluctuating noise and interfering speech on the speech-reception threshold for impaired and normal hearing," J Acoust Soc Am 88, 1725-1736.

Fu, Q. and Nogaki, G. (2005). "Noise susceptibility of cochlear implant users: the role of spectral resolution and smearing," J. Assoc. Res. Otolaryngol. 6, 19-27.

Fu, Q., Chinchilla, S., Nogaki, G. and Galvin, J.J.3. (2005). "Voice gender identification by cochlear implant users: the role of spectral and temporal resolution," J. Acoust. Soc. Am. 118, 1711-1718.

Fu, Q.J., Shannon, R.V. and Wang, X. (1998). "Effects of noise and spectral resolution on vowel and consonant recognition: acoustic and electric hearing," J Acoust Soc Am 104, 3586-3596.

Geurts, L. and Wouters, J. (2004). "Better place-coding of the fundamental frequency in cochlear implants," J. Acoust. Soc. Am. 115, 844-852.

Gifford, R. H., & J.K. Shallop, "Hearing preservation in patients with a cochlear implant," The ASHA Leader, vol. 12, No. 14, pp. 15, 17, 34 (Oct. 16, 2007).

Gifford, R.H. et al., "Effect of digital frequency compression (DFC) on speech recognition in candidates for combined electric and acoustic stimulation (EAS)," Journal of Speech Language and Hearing Research, vol. 50, Issue 5, pp. 1194-1202 (Oct. 2007).

Grant, K.W., Ardell, L.H., Kuhl, P.K. and Sparks, D.W. (1985). "The contribution of fundamental frequency, amplitude envelope, and voicing duration cues to speechreading in normal-hearing subjects," J Acoust Soc Am 77, 671-677.

(56) References Cited

OTHER PUBLICATIONS

Green, T., Faulkner, A. and Rosen, S. (2004). "Enhancing temporal cues to voice pitch in continuous interleaved sampling cochlear implants," J. Acoust. Soc. Am. 116, 2298-2310.
Green, T., Faulkner, A., Rosen, S. and Macherey, O. (2005). "Enhancement of temporal periodicity cues in cochlear implants: effects on prosodic perception and vowel identification," J. Acoust. Soc. Am. 118, 375-385.
Hall, J.W. and Wood, E.J. (1984). "Stimulus duration and frequency discrimination for normal-hearing and hearing-impaired subjects," J. Speech. Hear. Res. 27, 252-256.
Healy, E.W. and Steinbach, H.M. (2007). "The effect of smoothing filter slope and spectral frequency on temporal speech information," J Acoust Soc Am 121, 1177-1181.
Hillenbrand, J., Getty, L.A., Clark, M.J. and Wheeler, K. (1995). "Acoustic characteristics of American English vowels," J. Acoust. Soc. Am. 97, 3099-3111.
Holt, L.L., Lotto, A.J. and Kluender, K.R. (2001). "Influence of fundamental frequency on stop-consonant voicing perception: a case of learned covariation or auditory enhancement?," J. Acoust. Soc. Am. 109, 764-774.
Hopkins, K. and Moore, B.C.J. (2007). "Moderate cochlear hearing loss leads to a reduced ability to use temporal fine structure information," J Acoust Soc Am 122, 1055-1068.
Hopkins, K., Moore, B.C.J. and Stone, M.A. (2008). "Effects of moderate cochlear hearing loss on the ability to benefit from temporal fine structure information in speech," J Acoust Soc Am 123, 1140-1153.
Houtgast, T. and Festen, J.M. (2008). "On the auditory and cognitive functions that may explain an individual's elevation of the speech reception threshold in noise," Int J Audiol 47, 287-295.
Kishon-Rabin, L., Boothroyd, A. and Hanin, L. (1996). "Speechreading enhancement: a comparison of spatial-tactile display of voice fundamental frequency (F0) with auditory F0," J Acoust Soc Am 100, 593-602.
Kong, Y., Stickney, G.S. and Zeng, F. (2005). "Speech and melody recognition in binaurally combined acoustic and electric hearing," J. Acoust. Soc. Am. 117, 1351-1361.
Kong, Y.-Y. and R.P. Carlyon, "Improved speech recognition in noise in simulated binaurally combined acoustic and electric stimulation" J. Acoust. Soc. Am. vol. 121, No. 6, pp. 3717-3727 (Jun. 2007).
Laneau, J., Wouters, J. and Moonen, M. (2004). "Relative contributions of temporal and place pitch cues to fundamental frequency discrimination in cochlear implantees," J. Acoust. Soc. Am. 116, 3606-3619.
Li, N. and Loizou, P.C. (2008). "A glimpsing account for the benefit of simulated combined acoustic and electric hearing," J. Acoust. Soc. Am. 123, 2287-2294.
Liu, S., Del Rio, E., Bradlow, A.R. and Zeng, F. (2004). "Clear speech perception in acoustic and electric hearing," J. Acoust. Soc. Am. 116, 2374-2383.
Loizou, P.C. (1998). "Mimicking the Human Ear," IEEE Sig. Proc. Mag, Signal Processing Magazine, IEEE in Signal Processing Magazine, IEEE, vol. 15, No. 5. (1998), pp. 101-130.
Lorenzi, C., Debruille, L., Garnier, S., Fleuriot, P. and Moore, B.C.J. (2009). "Abnormal processing of temporal fine structure in speech for frequencies where absolute thresholds are normal," J Acoust Soc Am 125, 27-30.
Lorenzi, C., Gilbert, G., Carn H., Garnier, S. and Moore, B.C.J. (2006). "Speech perception problems of the hearing impaired reflect inability to use temporal fine structure," Proc Natl Acad Sci U S A 103, 18686-18869.
McDermott, H.J. and McKay, C.M. (1994). "Pitch ranking with nonsimultaneous dual-electrode electrical stimulation of the cochlea," J Acoust Soc Am 96, 155-162.
Milczynski, M., Wouters, J. and van Wieringen, A. (2009). "Improved fundamental frequency coding in cochlear implant signal processing," J Acoust Soc Am 125, 2260-2271.
Miller, G.A. and Licklider, J.C.R. (1950). "The Intelligibility of Interrupted Speech," J Acoust Soc Am 22, 167-173.

Miyoshi, S., Iida, Y., Shimizu, S., Matsushima, J. and Ifukube, T. (1996). "Proposal of a new auditory nerve stimulation method for cochlear prosthesis," Artif Organs 20, 941-946.
Moore, B.C.J. (2008). "The role of temporal fine structure processing in pitch perception, masking, and speech perception for normal-hearing and hearing-impaired people," J Assoc Res Otolaryngol 9, 399-406.
Moore, B.C.J., (2003), "Coding of Sounds in the Auditory System and Its Relevance to Signal Processing and Coding in Cochlear Implants," Otology & Neurotology 24: 243-254.
Nelson, P.B. and Jin, S. (2004). "Factors affecting speech understanding in gated interference: cochlear implant users and normal-hearing listeners," J. Acoust. Soc. Am. 115, 2286-2294.
Nelson, P.B., Jin, S., Carney, A.E. and Nelson, D.A. (2003). "Understanding speech in modulated interference: cochlear implant users and normal-hearing listeners," J. Acoust. Soc. Am. 113, 961-968.
Oxenham, A.J. and Simonson, A.M. (2009). "Masking release for low- and high-pass-filtered speech in the presence of noise and single-talker interference," J Acoust Soc Am 125, 457-468.
Peters, R.W., Moore, B.C.J. and Baer, T. (1998). "Speech reception thresholds in noise with and without spectral and temporal dips for hearing-impaired and normally hearing people," J Acoust Soc Am 103, 577-587.
Peterson, G.E. and Barney, H.L. (1952). "Control Methods Used in a Study of the Vowels," J. Acoust. Soc. Am. 24, 175-184.
Plomp, R. (1978). "Auditory handicap of hearing impairment and the limited benefit of hearing aids," J Acoust Soc Am 63, 533-549.
Plomp, R. (1986). "A signal-to-noise ratio model for the speech-reception threshold of the hearing impaired," J Speech Hear Res 29, 146-154.
Plomp, R. (1994). "Noise, amplification, and compression: considerations of three main issues in hearing aid design," Ear Hear 15, 2-12.
Press Release: "Clinical trial of combination hearing aid-cochlear implant device opens at UNC", http://www.unc.edu/news/archives/may07/cochlear050407.html (May 4, 2007), accessed Sep. 16, 2009, 2 pages.
Qin, M.K. and Oxenham, A.J. (2003). "Effects of simulated cochlear-implant processing on speech reception in fluctuating maskers," J. Acoust. Soc. Am. 114, 446-454.
Qin, M.K. and Oxenham, A.J. (2005). "Effects of envelope-vocoder processing on F0 discrimination and concurrent-vowel identification," Ear Hear. 26, 451-460.
Qin, M.K. and Oxenham, A.J. (2006). "Effects of introducing unprocessed low-frequency information on the reception of envelope-vocoder processed speech," J. Acoust. Soc. Am. 119, 2417-2426.
Rosen, S.M., Fourcin, A.J. and Moore, B.C.J. (1981). "Voice pitch as an aid to lipreading," Nature 291, 150-152.
Shannon, R.V., Zeng, F.G., Kamath, V., Wygonski, J. and Ekelid, M. (1995). "Speech recognition with primarily temporal cues," Science 270, 303-304.
Spitzer, S.M., Liss, J.M. and Mattys, S.L. (2007). "Acoustic cues to lexical segmentation: a study of resynthesized speech," J. Acoust. Soc. Am. 122, 3678-3687.
Stickney, G.S., Assmann, P.F., Chang, J. and Zeng, F. (2007). "Effects of cochlear implant processing and fundamental frequency on the intelligibility of competing sentences," J Acoust Soc Am 122, 1069-1078.
Stickney, G.S., Zeng, F., Litovsky, R. and Assmann, P. (2004). "Cochlear implant speech recognition with speech maskers," J. Acoust. Soc. Am. 116, 1081-1091.
Stone, M.A., Füllgrabe, C. and Moore, B.C.J. (2008). "Benefit of high-rate envelope cues in vocoder processing: effect of number of channels and spectral region," J Acoust Soc Am 124, 2272-2282.
Summers, V. and Leek, M.R. (1998). "F0 processing and the separation of competing speech signals by listeners with normal hearing and with hearing loss," J Speech Lang Hear Res 41, 1294-1306.
Turner, C.W., Gantz, B.J., Vidal, C., Behrens, A. and Henry, B.A. (2004). "Speech recognition in noise for cochlear implant listeners: benefits of residual acoustic hearing," J. Acoust. Soc. Am. 115, 1729-1735.

(56) References Cited

OTHER PUBLICATIONS

Vermiere, K. et al., "The Influence of Different Speech Processor and Hearing Aid Settings on Speech Perception Outcomes in Electric Acoustic Stimulation Patients Ear and Hearing", vol. 29, No. 1, pp. 76-86 (Jan. 2008).

Wei, C., Cao, K. and Zeng, F. (2004). "Mandarin tone recognition in cochlear-implant subjects," Hear. Res. 197, 87-95.

Whalen, D.H., Abramson, A.S., Lisker, L. and Mody, M. (1993). "F0 gives voicing information even with unambiguous voice onset times," J Acoust Soc Am 93, 2152-2159.

Whitmal, N.A., Poissant, S.F., Freyman, R.L. and Helfer, K.S. (2007). "Speech intelligibility in cochlear implant simulations: Effects of carrier type, interfering noise, and subject experience," J. Acoust. Soc. Am. 122, 2376-2388.

Wilson, B., Sun, X., Schatzer, R. and Wolford, R. (2004). "Representation of fine structure or fine frequency information with cochlear implants," International Congress Series 1273, 3-6.

Zhang, T. et al. (2010), "Information from the voice fundamental frequency (F0) region accounts for the majority of the benefit when acoustic stimulation is added to electric stimulation," Ear Hear. 31(1):63-9.

Fu, Q.-J. et al., "Auditory Training with Spectrally Shifted Speech: Implications for Cochlear Implant Patient Auditory Rehabilitation," JARO 6: 180-189, Jun. 2005.

* cited by examiner

DELIVERING FUNDAMENTAL FREQUENCY AND AMPLITUDE ENVELOPE CUES TO ENHANCE SPEECH UNDERSTANDING

CROSS-REFERENCE TO RELATED APPLICATIONS

This application is a continuation of and claims priority to U.S. patent application Ser. No. 12/433,851, entitled "Delivering Fundamental Frequency and Amplitude Envelope Cues to Enhance Speech Understanding," filed on Apr. 30, 2009, which claims priority to U.S. provisional patent application No. 61/049,349, entitled "Tone Modulation for Enhanced Speech Understanding" filed on Apr. 30, 2008. The entire contents of the above applications are incorporated herein by reference.

STATEMENT REGARDING FEDERALLY SPONSORED RESEARCH

This invention was made with government support under grant nos. DC 01376 and DC008329 awarded by the National Institute of Deafness and Other Communication Disorders. The government has certain rights in the invention.

BACKGROUND

This specification relates to enhancing speech understanding, particularly in individuals with cochlear implants who possess limited residual acoustic hearing.

Individuals with residual hearing restricted to the low frequencies (below about 500 Hz-750 Hz) have been implanted with a relatively short electrode array designed to preserve as much of the residual hearing as possible in the apical region. These individuals, in addition to full-insertion implant users who have some residual hearing in the unimplanted ear, have the potential to combine the electric and acoustic sources of information. For both simulated and real implant processing, the addition of low frequency acoustic stimulation often enhances speech understanding, particularly when listening to speech in the presence of competing speech. The benefit of this electric-acoustic stimulation (EAS) occurs even when the acoustic stimulation alone provides little or no intelligibility.

It has been suggested that listeners combine the relatively weak pitch information conveyed by the electric stimulation with the strong pitch cue from the target talker's fundamental frequency (F0) or voice pitch in the low-frequency acoustic region to segregate target and background. Further, it has been found that F0 aids in the segregation of competing talkers and that mean F0 differences between target and masker aid speech understanding with EAS, but not with electrical stimulation alone. F0 has also been shown to likely play an important role independent of any role that the first formant may play: the addition to vocoder stimulation of 300-Hz low-pass speech improved speech intelligibility in a competing background.

SUMMARY

This specification describes delivering fundamental frequency and amplitude envelope cues to enhance speech understanding. The technologies described in this specification relate to evaluating directly the importance of F0 for EAS, the importance of the amplitude envelope of the acoustic stimulus in the EAS effect, as well as the importance of combining F0 and the amplitude envelope. In one example, the relative contributions of F0 and the amplitude envelope of speech to EAS are examined by replacing the low-frequency speech with a tone that was modulated in frequency to track the F0 of the speech. Other examples include examining the relative contributions of F0 and the amplitude envelope by replacing the low-frequency speech with a tone that was modulated in amplitude with the envelope of the low-frequency speech, replacing the low-frequency speech with a tone modulated both in frequency and in amplitude, and shifting down the frequency of the modulated tone.

In one aspect, a computer-implemented method to enhance speech understanding is described. The method includes receiving speech from a talker at a system including one or more computers. The speech includes audio signals. The method further includes extracting, at the system, a fundamental frequency from the audio signals. The extracted fundamental frequency is unique to the talker. The method also includes modulating at the system, a tone in frequency with the extracted fundamental frequency of the received speech, and delivering the modulated tone.

This, and other aspects can include one or more of the following features. The method can further include modulating, at the system, the tone in amplitude with an amplitude envelope of the received speech, providing the tone of the speech, modulated in frequency with the extracted fundamental frequency of the received speech, and in amplitude with the amplitude envelope of the received speech. The modulated tone is amplified prior to the delivering. The amplitude envelope can be obtained by half-wave rectification and low-pass filtering. The method can include modulating the tone of the speech in frequency with dynamic changes of the extracted fundamental frequency. The dynamic changes of the extracted fundamental frequency can be obtained using YIN algorithm.

Other aspects can include systems including processors and computer-readable media tangibly encoding instructions executable to cause the processors to perform the methods described above.

In another aspect, a cochlear implant system includes a cochlear implant, means for receiving speech from a talker that includes audio signals, means for extracting a fundamental frequency from the audio signals that is unique to the talker, means for modulating a tone in frequency with the extracted fundamental frequency of the received speech, and means for providing the modulated tone to the cochlear implant.

This, and other aspects, can include one or more of the following features. The cochlear implant system can further include means for modulating the tone in amplitude with an amplitude envelope of the received speech, and providing the tone of the speech, modulated in amplitude with the amplitude envelope. The amplitude envelope can be obtained by half-wave rectification and low-pass filtering of the received speech. The cochlear implant system can further include means for modulating the tone in frequency with dynamic changes to the extracted fundamental frequency. The dynamic changes of the extracted fundamental frequency can be obtained using YIN algorithm.

In another aspect, a system includes a first transformer to receive audio signals and transform the received audio signals into a frequency-domain representation, and a process operatively coupled to the transformer. The processor includes a frequency compression unit to perform frequency compression of the frequency-domain representation of the audio signal, and a frequency transposition unit operatively coupled to the frequency compression unit to perform frequency transposition of the frequency-domain representation of the audio signal on which the frequency compression has been performed. The system includes a second transformer operatively coupled to the processor to transform the compressed and transposed audio signals into a time-domain representation, and a transmitter operatively coupled to the second transformer to deliver the signals in the time-domain representation.

This, and other aspects, can include one or more of the following features. The system can further include an amplifier operatively coupled to the second transformer to amplify the signals in the time-domain representation. The system can further include a level control unit operatively coupled to the amplifier to control a level by which the amplifier amplifies the signals in the time-domain representation. The frequency compression can be applied to the frequency region in which the fundamental frequency of most talkers occurs. The frequency transposition can be applied such that the frequency region in which the fundamental frequency of most talkers occurs is audible to the user. The system can further include an audio transducing device to receive the signals in the time-domain representation delivered by the second transformer.

Particular implementations of the subject matter described in this specification can be implemented to realize one or more of the following potential advantages. Significant benefit can be observed with the addition of a tone carrying F0 or envelope cues. The combination of F0 and envelope cues can provide significantly more benefit than either cue alone. This improvement remains unaffected by the presence of a tone carrying F0 and envelope cues of a background talker. The target tone modulated in both frequency and amplitude can produce between 24 and 57 percentage points of improvement in intelligibility. The frequency of the tone can be shifted down by as much as 125 Hz with minimal or no decline in the amount of benefit it provides, as long as F0 variation is reduced to control for the possibility that downward excursions will move so low in frequency as to be inaudible. The voice fundamental frequency and amplitude envelope information provided to the individual, that are described here, are cues that have been shown to provide as much as 57 percentage points of benefit to speech intelligibility when combined with either real or simulated electric stimulation from a cochlear implant. This demonstrates the importance of F0 information for EAS, and indicates that significant information can be provided by a tone that tracks F0, envelope cues, or both.

The details of one or more implementations of the subject matter described in this specification are set forth in the accompanying drawings and the description below. Other features, aspects, and advantages will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
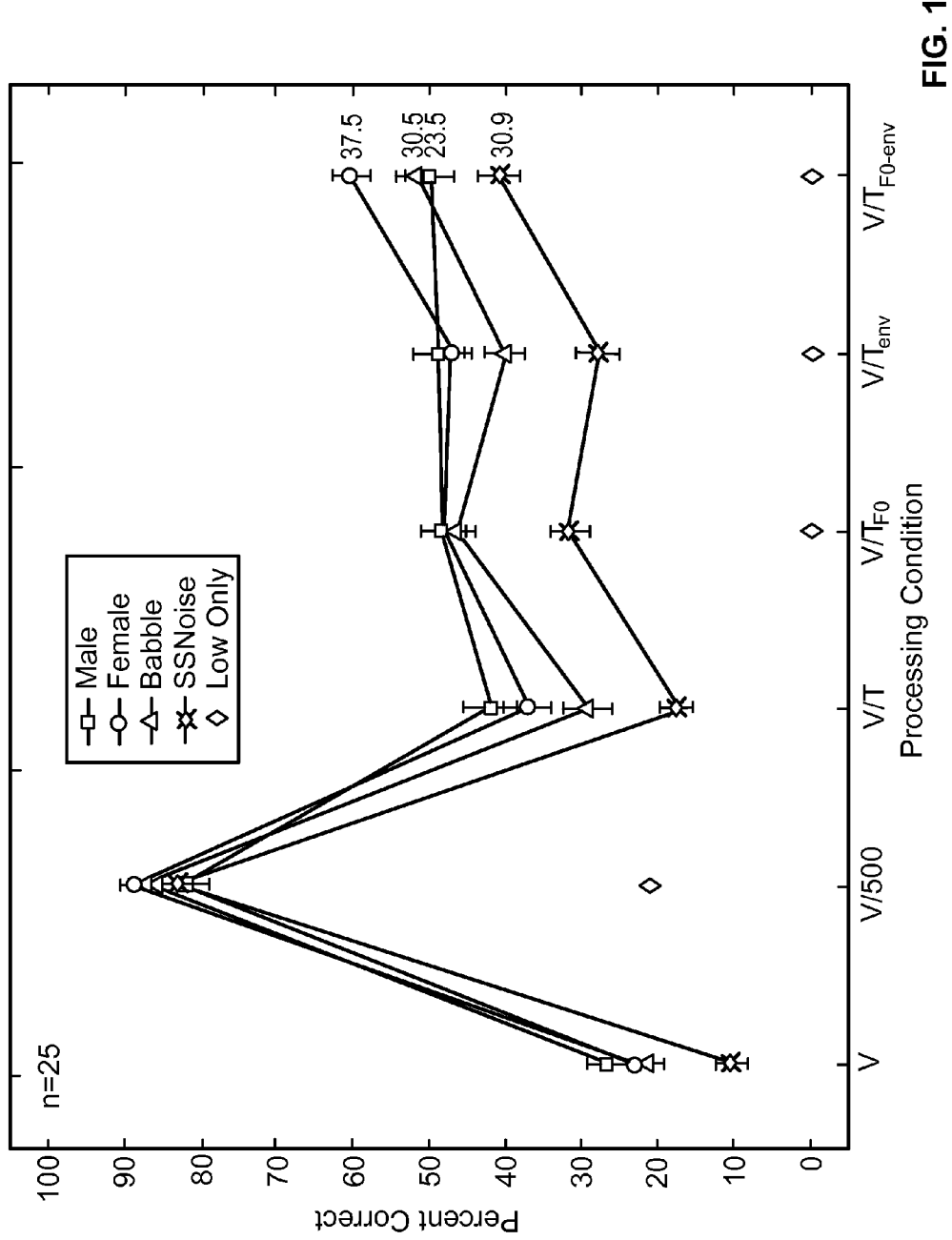
FIG. 1 is an example plot of mean percent correct scores obtained by replacing the low-pass speech with a tone that is modulated in frequency.

Individuals with residual hearing restricted to low frequencies are candidates for electric-acoustic stimulation (EAS). When low-frequency acoustic information is added to either real or simulated high-frequency electric stimulation, speech recognition often improves dramatically. This reflects the availability of fundamental frequency, F0, information in the acoustic region. This specification describes methods to determine the contributions of F0, as well as amplitude envelope cues to speech intelligibility in simulated EAS.

In simulated EAS, the low-pass speech was replaced with a tone having a frequency equal to that of the target talker's mean F0, e.g., 184 Hz. By applying to the tone, the dynamic changes in F0, the amplitude envelope of the low-pass speech, or both, the relative contributions of each cue to intelligibility were assessed. If EAS benefit can be demonstrated with a low-frequency tone carrying F0, and/or the amplitude envelope, it is possible that impaired listeners with especially elevated low-frequency thresholds can benefit more from the tonal cue than from speech itself because it may be easier to make the entire narrow band cue more audible than the broader band speech.

In some implementations, the contribution of the dynamic changes in F0 to the benefit in intelligibility from simulated EAS is examined by replacing the low-pass speech with a tone that is modulated in frequency to track the changes in F0 that occur across an utterance. In some implementations, the above implementation can include conditions in which a tone equal to the mean F0 of the target talker is modulated by the amplitude envelope of the low-pass target speech because the amplitude envelope of the low-pass speech is expected to contribute to intelligibility as well. In some implementations, an additional set of conditions combines the F0 and the envelope cues.

Data was collected from 25 fluent speakers of English (15 females, 10 males), who ranged in age from 26 to 38 years. All 25 listeners had pure-tone air-conduction thresholds≤20 dBL HL (ANSI, 1996) at octave and half-octave frequencies from 250 Hz to 6000 Hz in the right ear, which was used exclusively. Prior to testing, the dynamic changes in the target talker's F0 were extracted from each sentence using the YIN algorithm with a 40 ms window size and 10 ms raised-cosine ramps applied to the transitions. It should be noted that other algorithms to extract F0, such as those based on the zero-crossings in the time-domain waveform, or on the ratio of harmonic components in the frequency-domain representation of the signal, can be used as well.

Target stimuli consisted of the IEEE sentences (IEEE, 1969) produced by a female talker with a mean fundamental frequency of 184 Hz. Backgrounds were the AZBIO sentences produced by a male (mean F0=92 Hz) or a female (mean F0=224 Hz) talker, 4-talker babble, or generic speech-shaped noise (low-passed at 800 Hz, using a 1st order Butterworth filter). The target speech began 150 ms after the onset of the background and ended 150 ms before the background offset. Two single-talker background sentences were concatenated when necessary. Prior to processing, the level of the target speech was adjusted to 70 dB Sound Pressure Level (SPL) and the value of the root mean square (RMS) level of the background stimuli was adjusted to achieve a +10 dB signal-to-noise-ratio, which was shown in pilot testing to produce about 30% correct in vocoder-only test conditions.

Electric stimulation was simulated using a 4-channel vocoder that employed sinusoidal carriers. The signal was band-pass filtered into four frequency bands. The logarithmically spaced cutoff frequencies of the contiguous vocoder bands were 750 Hz, 1234 Hz, 2031 Hz, 3342 Hz, and 5500 Hz. The envelope of each band was extracted by half-wave rectification and low-pass filtering (6th order Butterworth, cutoff frequency of 400 Hz or half the bandwidth, which ever was less). This envelope was used to modulate the amplitude of a tone at the arithmetic center of the band (the frequencies of the carrier tones were 992 Hz, 1633 Hz, 2687 Hz, and 4421 Hz). This simulates a 20 mm insertion depth, which is appropriate for EAS in a single ear.

The low-frequency region consisted of either target speech low-passed at 500 Hz (10th order Butterworth) or a tone equal to the mean F0 of the target talker for each sentence (overall mean F0=184 Hz). The tone was unmodulated, or modulated either in frequency with the dynamic F0 changes in each target utterance, in amplitude with the envelope of the 500 Hz low-pass speech, obtained via half-wave rectification and low-pass filtering at 16 Hz (2nd order Butterworth), or both, in frequency and amplitude. In all cases, the voicing track was applied to the tone, and the level of the tone was adjusted to be equal in RMS to that of the 500 Hz low-pass speech. The processing can be done digitally using software routines, e.g., those available in Matlab. Stimuli can be presented using instruments, for example, Echo Gina 3G sound card (16 bit precision, 44.1 kHz sampling rate), Tucker Davis PA5 attenuators, and Sennheiser HD250 headphones.

The 4-channel vocoder (target plus background) was either presented alone (V), combined with the 500 Hz low-pass target speech (V/500), or combined with a tone that was either unmodulated (except for voicing, V/t), modulated in frequency by the dynamic change in F0 (V/$T_{F0}$), modulated in amplitude by the envelope of the low-pass speech (V/$T_{env}$), or modulated in both frequency and amplitude (V/$T_{F0-env}$). In addition, the 500 Hz low-pass target speech and each of the tonal cues were presented in isolation without the vocoder stimulation.

As mentioned previously, the voice data for modulation was collected from 25 participants. The participants were seated in a double-walled sound booth with an experimenter, who scored responses and controlled stimulus presentation. Responses were made verbally, and participants were instructed to repeat as much of the target sentence as they could. No feedback was provided. Participants first heard 10 unprocessed broadband target sentences presented in quiet, followed by 10 sentences in quiet processed with the 4-channel vocoder, to become familiar with the target talker's voice and with the vocoder processing. In addition, pilot data indicated a learning effect for the vocoder-plus-tone conditions, with an asymptote at about 80 sentences. As a result, prior to testing, participants heard 100 sentences of the target talker processed through the 4-channel vocoder, combined with the low-frequency tone modulated in both frequency and amplitude (V/TF50-env). There were 50 keywords (10 sentences) per test condition, and the presentation order of the conditions was randomized for each subject. No sentence was heard more than once.

FIG. 1 shows the mean percent correct results. Each curve represents performance in a different background, and error bars represent ±1 standard error. The different processing conditions are represented along the X axis. The diamond symbols represent performance when the respective low-frequency was presented alone. A 2-factor repeated-measures analysis of variance, with background and processing conditions as the main effects, revealed significant differences ($p<0.001$) within each variable. A post-hoc Tukey analysis on the background variable showed all pairwise differences to be significant except male and female, and male and babble. A Tukey analysis was conducted on the different processing conditions as well; significant differences ($p<0.001$) were found between each pair of groups, except V/$T_{F0}$ and V/$T_{env}$.

The improvement in performance observed from the V (vocoder only) conditions to the V/500 (vocoder plus 500 Hz low-pass speech) conditions demonstrates the EAS effect of combining vocoder stimulation with low-frequency speech, which itself provided only about 20% intelligibility, as shown by the diamond marker at V/500 in FIG. 1. The improvement in performance over V in the V/T (vocoder plus tone carrying the voicing cue only) conditions averaged about 11 percentage points across backgrounds. This effect indicates that the voicing cue is informative under these conditions. The effect of the dynamic changes in F0 on intelligibility can be seen by comparing V/T with V/$T_{F0}$. Across backgrounds, the improvement averaged about 13 percentage points. Similarly, the addition of a tone modulated with the envelope of the low-pass target speech to vocoder (V/$T_{env}$) produced about 11 percentage points of improvement relative to V/T. Both of these differences were statistically significant ($p<0.001$). Finally, when the tone was modulated in both frequency and amplitude, and combined with vocoder (V/$T_{F0-env}$), improvement over V/T averaged about 20 percentage points. The tonal cues, by themselves, provide no intelligibility, as can be seen by the diamond symbols at V/$T_{F0}$, V/$T_{env}$, and V/$T_{F0-env}$).

For three of the four backgrounds (female talker, babble, and speech-shaped noise), the contributions to intelligibility of F0 and the amplitude envelope of low-pass speech were statistically equivalent ($p>0.42$), and each cue was statistically greater than the voicing cue alone. In addition, in these backgrounds, the combination of F0 and amplitude envelope cues provided significant benefit over the amplitude envelope cue alone ($p<0.01$).

The amount of improvement in the V/$T_{F0-env}$ condition relative to the V condition for each background is shown in FIG. 1. The largest improvement was seen in the female background (38 percentage points), while the amount of improvement was 24 percentage points in the male background, and about 31 percentage points in both the multi-talker babble and speech-shaped noise backgrounds. When the background was a male talker, nearly all of the benefit over vocoder only provided in the tone conditions was due to the voicing cue. Neither F0, nor the amplitude envelope, nor the combination of the two cues provided significantly more benefit than voicing alone.

For three of the four backgrounds (female talker, babble, and speech-shaped noise), the pattern of results was similar, i.e., F0 and the amplitude envelope of low-pass speech contributed equal, and somewhat independent and additive sources of information. In addition, the F-cue alone provided significant benefit over the voicing cue, demonstrating that F0 is a useful cue in simulated EAS conditions. While voicing provided a significant benefit over vocoder only, it was significantly less than the benefit provided by either F0 alone or the envelope alone. Further, performance with the male background showed a pattern of results wherein nearly all of the improvement observed in the tone conditions can be attributed to the voicing cue. This pattern of results observed for the male background can be attributed to the various procedural differences, e.g., sentence materials, number of vocoder channels, carrier type in the low-frequency region, and the like, that may contributes to the different pattern of results in the two studies.

The results provide direct evidence for the importance of F0 in simulated EAS. There was a significant contribution to intelligibility from the envelope cue. Spectrographic representation of the V/T and V/T$_{env}$ processing conditions reveal co-modulation among the vocoder bands and the low-frequency tone. Coherent envelope fluctuations facilitate the integration or grouping of spectrally dispersed frequency bands into a single auditory object, and can provide a release from masking. In addition, a release from masking for speech stimuli is available when noise-band maskers are co-modulated, but this phenomenon is observed for speech detection only, and not for recognition. Further, it is plausible that the envelope in the low-frequency region improves speech intelligibility by enhancing the segregation of the target from background speech in the vocoder region.

The techniques described so far demonstrate a benefit in intelligibility due to the presence of F0 in simulated EAS, at least in three of four backgrounds tested. However, it is important to note that the background was never present in the low-frequency region in any of these conditions. This condition was chosen because of the use of a tonal low-frequency cue, wherein the presence of the background speech in the low-frequency region made hearing the tone difficult. Removing the background from the low-frequency region allowed a more direct comparison between performance when the tone with target modulation was present versus performance when the target speech itself was present. In subsequent portions of this specification, the effect of the presence of the background in the low-frequency region on the improvement due to the tone is described.

If the effects of F0 in simulated and real EAS are to aid segregation of target and masker, then it is possible that F0 information from a background will provide similar benefit. On the other hand, the presence of a background could impair performance. A third possibility is that there is no observable change in performance. Thus, it is desirable to determine whether the presence of a tone that carries the F0 of the background would aid performance. If the background F0 alone, i.e., without the target F0, provided a benefit in intelligibility, this would represent evidence that the improvement was due to segregation of the target and background. It is also desirable to examine the effect of F0 in the more ecologically valid situation in which both the target and background are present in the low-frequency region. In this case, the vocoder is combined with two tones, one carrying the F0 from the target, and one carrying the F0 from the background. The conditions in which the vocoder is combined with target and background low-pass speech are included as well, to allow for direct comparison. Because the amplitude envelope is present when low-pass speech is the low-frequency cue, the amplitude envelope of the low-pass target or background speech was applied to the respective tone as well. Thus, previously described experiments were replicated, and additionally, extended with the low-frequency stimulus representing either the target or the background (low-pass background speech or a tone tracking the F0 and amplitude envelope of the background speech). Conditions in which both the target and background were present, e.g., both as low-pass filtered speech signals or both as tones tracking their respective F0 and amplitude envelope, were also included because of the ecological validity of these manipulations.

For this implementation, data was collected from twelve participants. Twelve normal-hearing listeners (11 females, 1 male) ranging in age from 26 to 38 years were paid an hourly wage for their services. The criteria for inclusion were identical to experiment 1, although a different group of listeners was recruited. The stimuli, processing, and hardware can be identical to that used in the previously described experiments. In some implementations, the CUNY sentences produced by a male talker (mean F0=127 Hz) can be used as target stimuli, and the IEEE sentences produced by either the target female in experiment 1 or a male (mean F0=90 Hz) can be used as backgrounds.

A target sentence is combined with a background and processed through a 4-channel vocoder, as described previously. The vocoder stimulation is presented either alone (V) or with a low-frequency cue. In three conditions, the low-frequency cue consisted of 500 Hz low-pass speech, and was either target speech alone (V/S500), background speech alone (V/B500), or both target and background speech (V/SB500). Three other conditions combined the vocoder with either a tone that was modulated in frequency with the target talker's F0 and amplitude with the envelope of the 500 Hz low-pass target speech (V/S$_{f0-env}$), a tone modulated in the same way using the background's F0 and low-pass envelope (V/B$_{F0-env}$), or both tones combined (V/SB$_{F0-env}$). In addition, the background was either a male or female talker.

Figure 2:
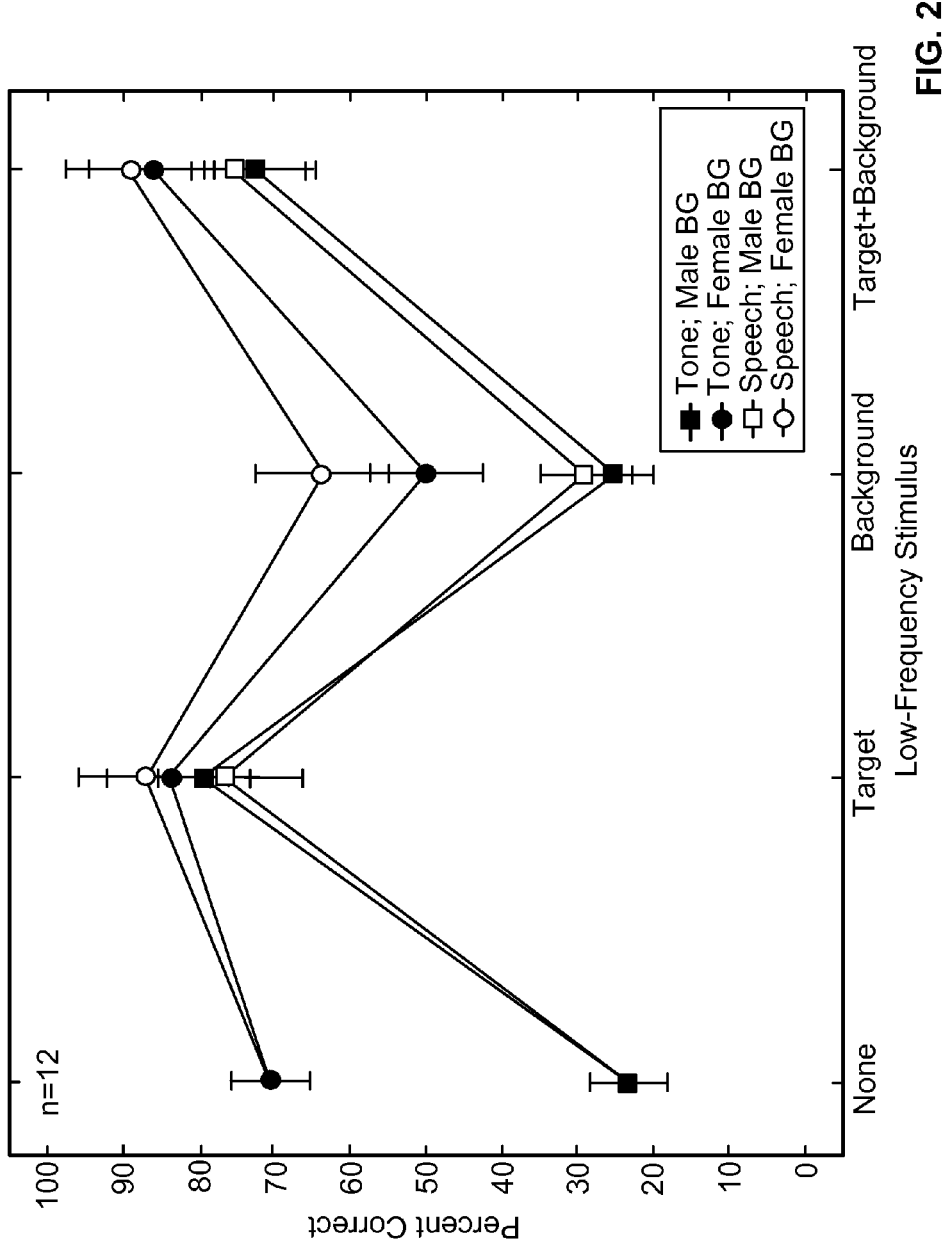
FIG. 2 is an example plot of mean correct scores obtained by replacing the low-pass speech with a tone that is modulated to account for background.

FIG. 2 shows the mean percent correct results. In FIG. 2, circles represent performance with a female background and squares represent performance with a male background. Unfilled symbols represent performance when speech is present in the low-frequency region and filled symbols represent performance when a tone or tones were present. The different target/background combination presented in the low-frequency region are represented along the X axis. There was either no stimulus (vocoder only: none), target only (target), background only (background), or both target and background (target+background). Error bars represent ±1 standard error.

A 3-factor repeated-measures analysis of variance was conducted, with background gender (male or female), low-frequency stimulus (none, target background, or target+background), and low-frequency processing (tone or speech) conditions as the main effects. There were significant differences within the stimulus and gender variables (p<0.001). Neither the three-way interaction nor any of the two-way interactions were statistically significant (p>0.42), except the interaction between gender and low-frequency stimulus (p=0.001). This significant interaction is likely due to the differences in performance observed in the vocoder-only conditions (none), which showed the male background to be a more effective masker than the female background. The processing variable was not significant (p=0.22). The lack of a significant difference for processing indicates that a tone conveying both the F0 and the envelope of the target speech provided as much benefit as the low-pass speech itself, whether or not the background was present.

A post-hoc Tukey analysis was conducted on group means. Within the male background, the presence of the target in the low-frequency region (speech or tone) provided significant improvement over vocoder alone, regardless of whether the background was present (target+background) or not (target) (p<0.001). On the other hand, the background (speech or tone) has no statistically significant effect on intelligibility, regardless of whether or not the target was present (target+background) or not (background) (p>0.99). Within the female background, there were no statistically significant changes in intelligibility due to either the target or the background, whether the low-frequency stimulus was speech or tones.

For the most part, the presence of the background in the low-frequency region had no statistically significant effect on performance. In other words, performance was equivalent whether the background was present or not. This can be seen by comparing performance in 'none' with the performance in 'background,' and performance in 'target' with performance in 'target+background.' The one exception was in the female-background (V/SB$_{F0-env}$) condition, where performance declined by about 20 percentage points from vocoder only. When the background was a female talker (circles in FIG. 2), the amount of improvement due to the low-frequency target stimulus (either speech or tone) was about 15 percentage points, while with the male background (squares in FIG. 2), which was a much more effective masker in the vocoder-only condition, the improvement in performance when a target stimulus was present in the low-frequency region was between 52 and 57 percentage points.

It has been suggested that F0 aids in segregating target from background in EAS. If the tone that tracked the F0 and amplitude envelope of the background talker had provided a benefit over vocoder only, this would have been clear evidence for segregation. It may be that F0 does, in fact, help segregate target from background, but that the salience of the background tone in the low-frequency region makes it difficult to attend to the target speech in the vocoder region when there is no corresponding target tone. Subjectively, the tone appears to fuse with the vocoder quite well, even when it is conveying background F0. The effect of the amplitude envelope also may be due to segregation.

The CUNY sentences (target materials) are considered to have high context, whereas the IEEE sentences are considered to have low context. It has been shown that the use of high-context sentence materials reduces the dynamic range of intelligibility as compared to low-context sentences, so that a given increase in the amount of acoustic information provided yields a correspondingly greater change in percent correct. This dynamic-range reduction may be responsible for the difference in the amount of improvement due to the tone observed between experiments. In the latter experiments, the improvement in performance due to the presence of the target tone in the low-frequency region was as much as 57 percentage points, whereas in the former experiments, this improvement was about 30 percentage points on average.

In contrast to the results of the former experiments, a tone carrying F0 and the low-frequency amplitude envelope of the target talker provided as much benefit as the low-pass target speech. Spectral analysis shows that when the CUNY sentences are low-pass filtered at 500 Hz, the first formant (F1), and to some extend the second formant (F2) are present. The results of the latter experiments seem to indicate that at least under these conditions, F1 is not necessary, and a tone carrying the dynamic changes in F0 and the amplitude envelope is sufficient for the full EAS effect.

Figure 3:
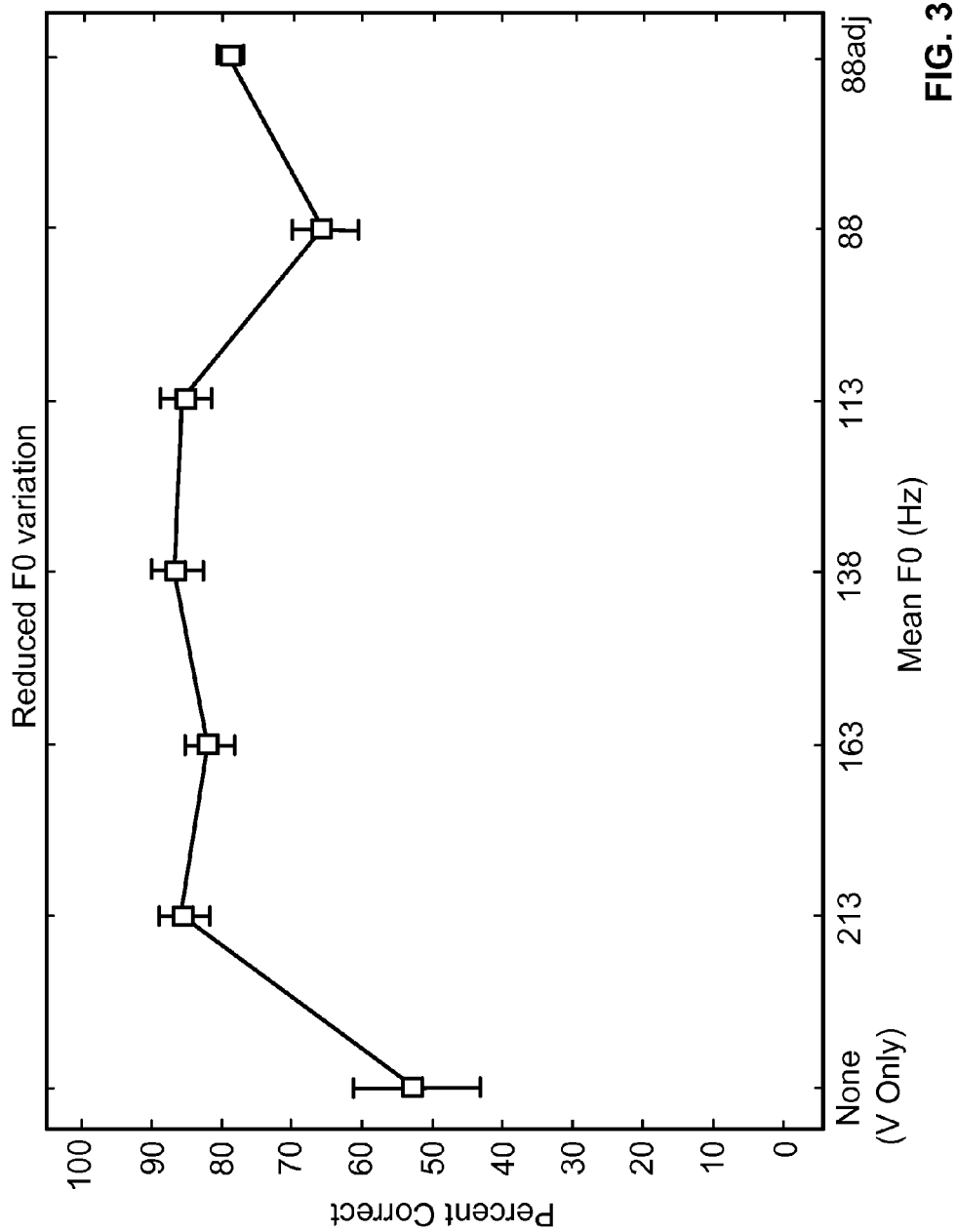
FIG. 3 is an example plot of modulated tone measured while shifting tone frequency downward, and reducing F0 variation.

FIG. 3 shows the benefit obtained by employing processing conditions in which the tone is shifted down in frequency and the F0 and amplitude envelope cues are delivered to an audible frequency region. By doing so, the EAS benefit can be achieved with the tone where none was possible otherwise. Such EAS benefit is valuable to CI patients who possess extremely limited low-frequency hearing. These patients may not show an EAS benefit typically because they do not possess enough residual low-frequency hearing. However, if the tone is shifted down in frequency and the F0 and amplitude envelope cues are delivered to an audible frequency region, these patients stand to gain the greatest EAS benefit. Thus, the benefits of the modulated tone were measured while shifting the frequency of the tone downward. 12 normal-hearing listeners participated. The modulated tone was shifted down in frequency by 0, 50, 75, 100, and 125 Hz. These shifts correspond to mean F0 values of 213 (the natural mean F0 of the female target talker used), 163, 138, 113, and 88 Hz. Because the F0 variation is typically greater for talkers with a higher mean, a condition was included that reduced the F0 variation at the 88 Hz mean F0. The results indicate that shifting the tone by as much as 100 Hz (the 113 mean F0 condition) had no effect on the benefits of the modulated tone. At a mean F0 of 88 Hz, a significant decline in benefit was observed, although the modulated tone at this mean F0 still provided significant benefit. However, the decline in benefit observed at 88 Hz disappeared when the F0 variation was reduced. These results have been confirmed with an implant patient, and demonstrate that if a patient does not have enough residual hearing to benefit from typical EAS, an effective solution is to transpose the F0 and amplitude envelope cues down in frequency to a region that is audible to the listener.

The results of these experiments demonstrate that F0 can be an important cue under simulated EAS learning. Both F0 and the amplitude envelope contributed significantly to the EAS benefit, and when these two cues were combined, a dramatic benefit of as much as 57 percentage points was observed over vocoder only. When sentence context was high, the presence of the tone provided as much benefit as low-pass speech, and this benefit was not adversely affected by the presence of a tone carrying the F0 and low-pass amplitude envelope of the background speech.

The EAS benefit provided by a tone carrying F0 and envelope cues holds promise for implant listeners, particularly those with a very low audiometric 'corner frequency' in the low-frequency region. These listeners may not benefit from a typical EAS configuration because of their inability to adequately hear the speech in the low-frequency region, even with amplification. Providing a means of delivering F0 and amplitude envelope cues to a frequency region that is audible to the patient can provide the benefits of EAS to these patients, who would otherwise not benefit. A processor can be configured to extract F0 in real time, and apply the extracted F0, as well as the amplitude envelope, to a tone in the low-frequency acoustic region. This approach is different from previous attempts at exploiting F0 information with electric stimulation. Such a processor will present F0 information in the acoustic region, which can be combined with electrical stimulation in the higher frequency region. Such a processor will greatly expand the population of cochlear implant users who stand to benefit from EAS to include individuals who have very little residual low-frequency hearing.

In conclusion, a tone modulated in frequency to track the F0 of the target talker provides significant benefit in simulated EAS. A tone modulated in amplitude to track the amplitude envelope of the target talker provides significant benefit in simulated EAS. A tone modulated in both frequency and amplitude (F0-env tone) generally provides more benefit than either cue alone. The presence of the F0-env tone, under these simulated conditions, resulted in improvements in intelligibility of between 23 and 57 percentage points. This benefit was not affected by the presence of a tone that tracked the F0 and low-frequency envelope of a background. The EAS benefit due to the F0-env tone seems to be greater when the target speech is highly contextual.

Experiments conducted with both CI listeners and with normal-hearing listeners in a simulation of CI listening showed that the modulated tone provided a significant benefit over electric-only stimulation. FIG. 3 is an example of a schematic of a pitch processor for performing the experiments described previously. The pitch processor can be applied in individuals whose low-frequency hearing is limited, i.e., their thresholds for detecting sounds are too high or their hearing does not extend to sufficiently high frequencies to benefit from EAS. The pitch processor can be configured to present all the low-frequency acoustic information at a frequency and level that can be heard.

An individual using this pitch processor will not simply receive an amplified acoustic signal from the environment, but rather one that is purely synthesized. This will allow for the ability to use signal processing techniques to tailor the characteristics of the stimulus to suit the particular user's hearing configuration.

The pitch processor can be used in several implementations. The method of stimulus delivery in each implementation can vary, depending on the user. In some implementations, amplifying the tone using current technology found in hearing aids will suffice. In some implementations, for example, implementations where users are more profoundly deaf in the low-frequency region, the pitch processor can be built as part of the CI processor, and the pitch information delivered electrically. In other implementations, two or three of the implanted electrodes can be positioned in the cochlea to stimulate the low-frequency region. Then, the phase and amplitude of the output of each electrode can be manipulated to steer the electrical current up or down to track the changes in pitch. This technique is known as current steering, and can elicit the percept of pitch change.

In general, the pitch processor is configured to deliver the F0 of a speaker in addition to the amplitude envelope of the speaker's voice. This frequency-modulated and amplitude-modulated signal can be delivered to individuals in a variety of ways, for example, acoustically, electrically, and the like.

Figure 4:
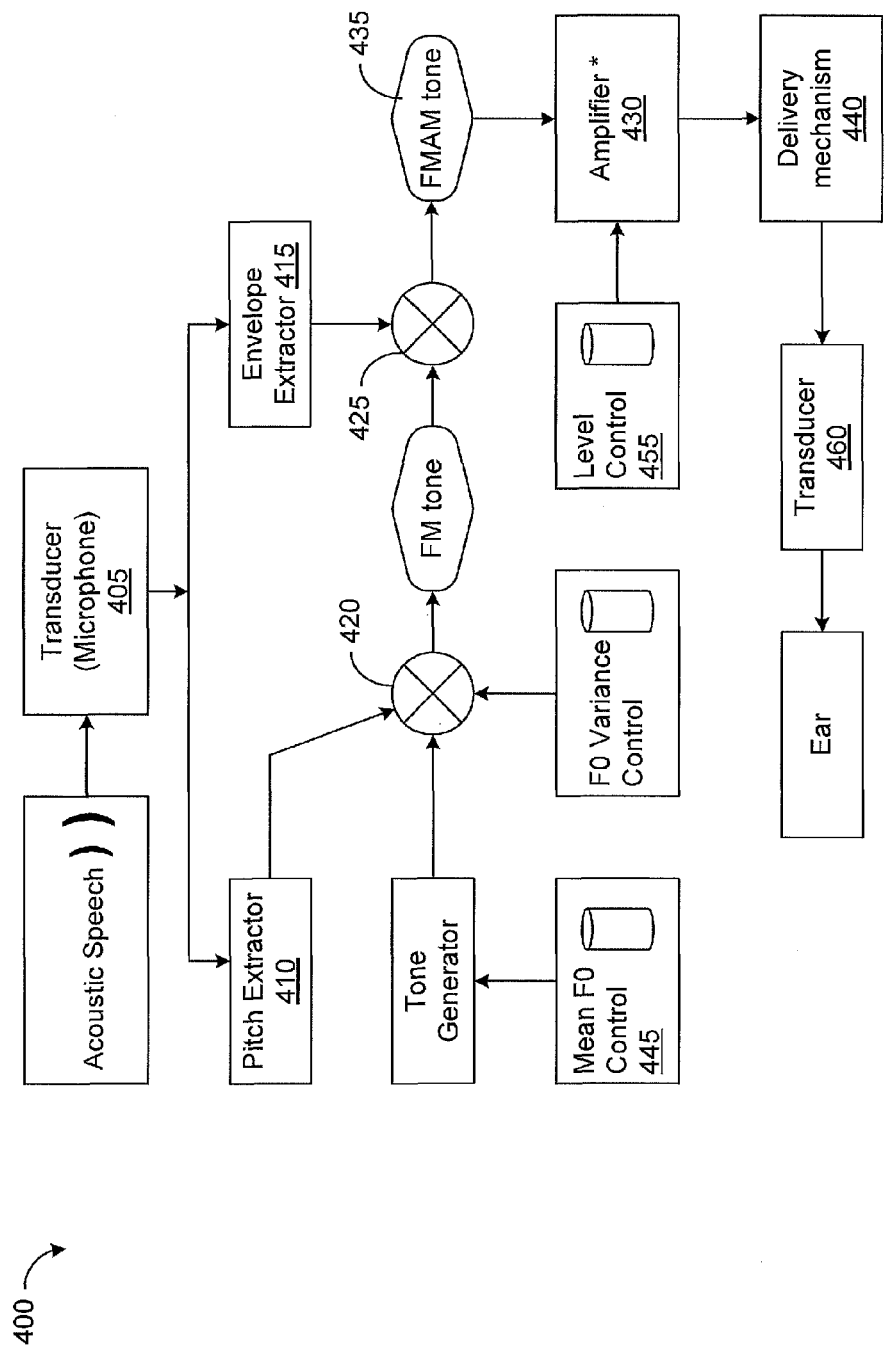
FIG. 4 is an example of a schematic of a pitch processor.

FIG. 4 is an example of a schematic of the pitch processor 400. The pitch processor 400 includes a transducer 405, which can be an audio transducing device, for example, a microphone, that transduces the incoming speech signal. The processor 400 includes a pitch extractor 410 to extract pitch information and an envelope extractor 415 to extract amplitude envelope information. The processor 400 includes a first modulator 420 to frequency-modulate a tone and a second modulator 425 to apply the amplitude envelope. The processor 400 includes an amplifier 430 to amplify the frequency-modulated and amplitude-modulated (FMAM) tone 435, and a delivery mechanism 440 to deliver the amplified tone to a destination transducer 460 that transduces the signal into audio prior to delivering the audio to the ear acoustically. For example, the delivery mechanism 440 is similar to the mechanism in a hearing aid. The processor 400 includes pitch control circuitry 445 and a variance control circuitry 450 to ensure that the frequency of the tone remains in an audible frequency region for the listener. The processor 400 also includes a level control 455 that is a volume potentiometer adjustable by the user.

In alternative implementations, the pitch processor 400 is configured to deliver pitch information by other methods. For example, rather than amplify the acoustic FMAM tone, the processor 400 can electrically deliver pitch information to the ear, for example, using two or three electrodes implanted into the user's cochlea to directly stimulate the auditory nerve. In such implementations, current steering or tri-polar stimulation can be employed to deliver the pitch information. Some or all steps of the pitch processor 400 can be implemented in hardware, software, firmware, and the like. In another implementation, the pitch processor 400 can deliver F0 and amplitude envelope information using frequency compression and transposition techniques. In such implementations, the frequency region encompassing the F0 of most talkers (100-250 Hz) is compressed and transposed down into a frequency region that is audible to the user (for example, 75-125 Hz). In such implementations, as an alternative to synthesizing a tone, the actual voice F0 of the target talker is made audible to the user. The processing required for such an implementation could be based on Fourier transforms, or others, such as wavelet transforms.

Figure 5:
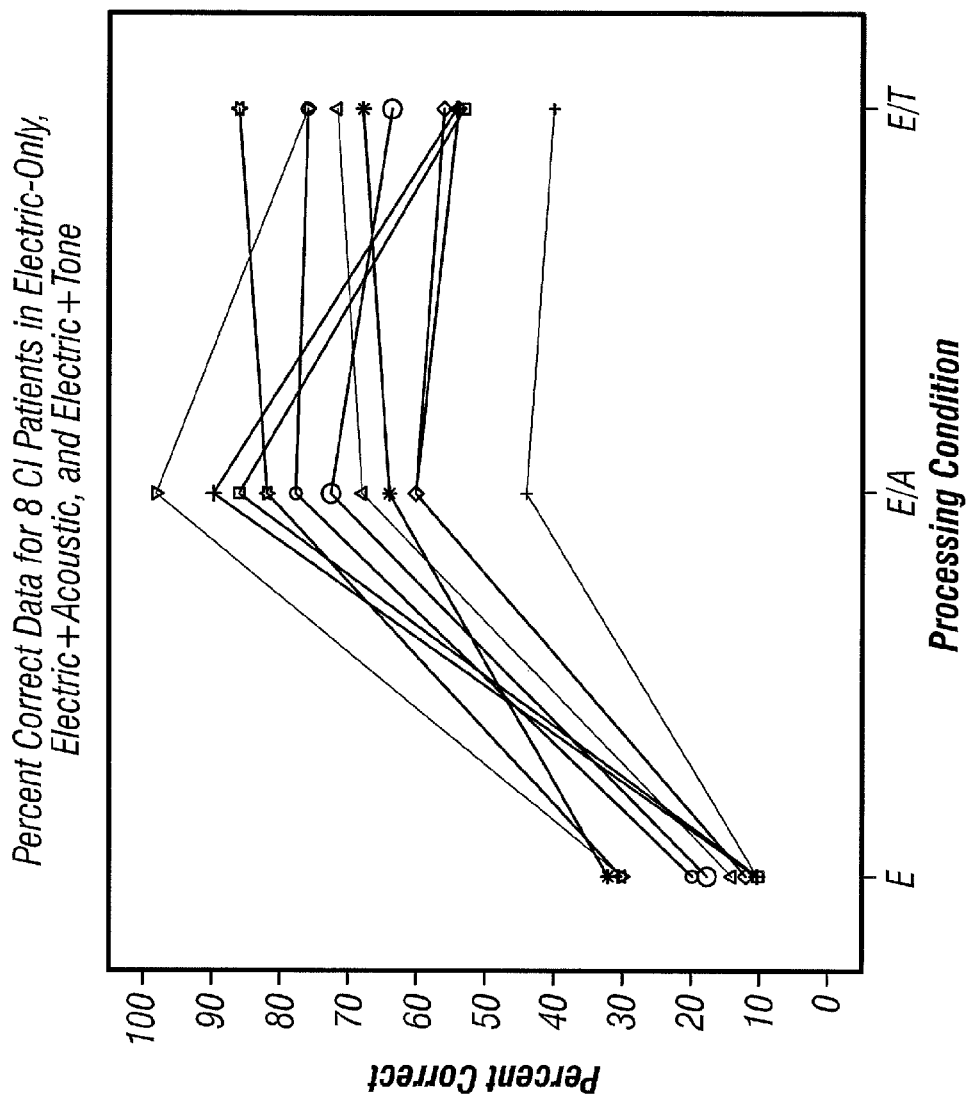
FIG. 5 is a plot of correct data versus processing condition.
Figure 6:
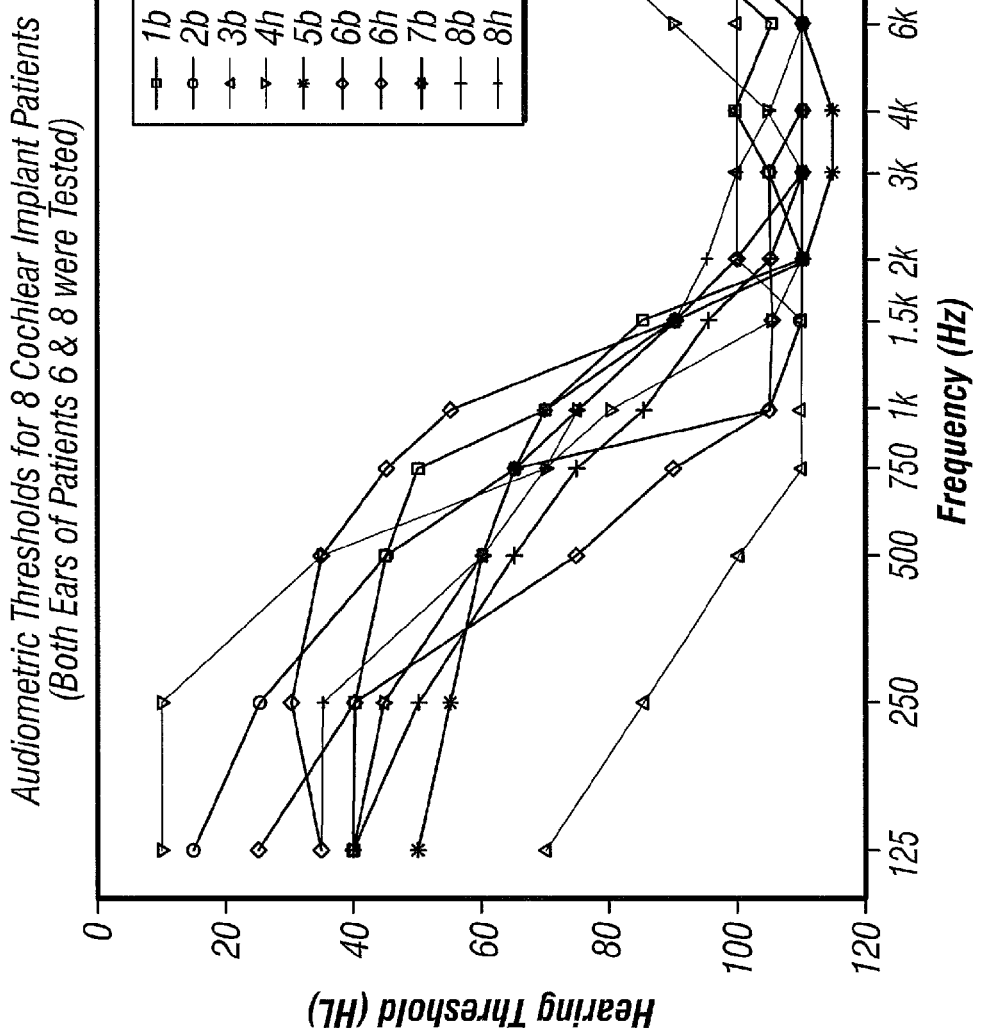
FIG. 6 is a plot of hearing threshold versus frequency.

FIG. 5 is a plot of percent correct data for eight cochlear implant patients in electric-only (E), electric+acoustic (E/A), and electric+tone (E/T) processing conditions. FIG. 6 is a plot of audiometric hearing thresholds for eight cochlear implant patients. Both ears of patients 6 and 8 were tested.

Figure 7:
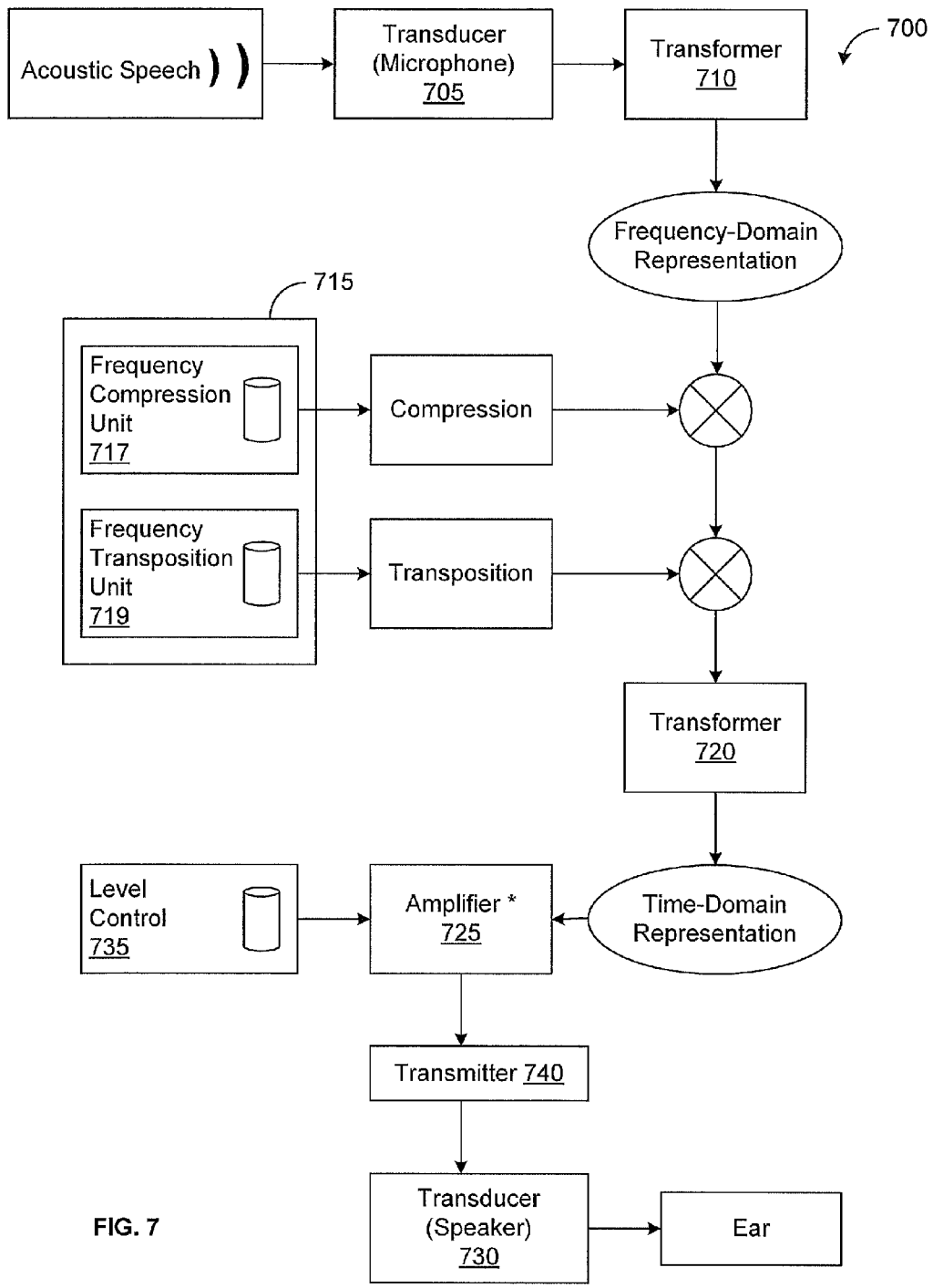
FIG. 7 is an example of a schematic of an alternative implementation of a pitch processing system.

FIG. 7 is an example of a schematic of an alternative implementation of a pitch processing system 700. The system 700 includes a first transformer 715 to transform audio signals into a frequency-domain representation, for example, using Fast Fourier Transformation. The first transformer 710 receives audio signals from a transducer 750, for example, a microphone, which, in turn, receives audio from a talker. The system 700 includes a processor 715 that is operatively coupled to the first transformer 710. The processor includes a frequency compression unit 717 and a frequency transposition unit 719. The frequency compression unit 717 performs frequency compression of the frequency-domain representation of the audio signal. The system 700 applies the frequency compression in the frequency region in which the fundamental frequency of most talkers occurs. The frequency transposition unit 719 performs frequency transposition of the frequency-domain representation of the audio signal on which the frequency compression has been performed. The system 700 applies the frequency transposition such that the frequency region in which the fundamental frequency of most talkers occurs is audible to the user, for example, the user with the CI implant. The system 700 further includes a second transformer 720 operatively coupled to the processor 715 to transform the compressed and transposed audio signals into a time-domain representation. An amplifier 725 is operatively coupled to the second transformer to amplify the signals in the time-domain representation. A level of amplification is controlled by a level control 735 connected to the amplifier 725. The amplified signals are transmitted to a transducer 730, for example, a microphone, by a transmitter 740 operatively coupled to the amplifier 725.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on a computer storage medium for execution by, or to control the operation of, data processing apparatus. A computer storage medium can be, or be included in, a computer-readable storage device, a computer-readable storage substrate, a random or serial access memory array or device, or a combination of one or more of them. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources. The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

While this specification contains many specific implementation details, these should not be construed as limitations on the scope of the invention or of what may be claimed, but rather as descriptions of features specific to particular implementations of the invention. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of various methods and systems have been described. Variations and enhancements of the described implementations and other implementations can be made based on what is described and illustrated. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous. In some implementations, the system can include a cochlear implant including a processor configured to perform the operations described. For example, the cochlear implant can be surgically implanted in a patient's ear. The cochlear implant can include a microphone to receive the speech from a talker. The processor included in the implant can include a pitch extractor to extract the fundamental frequency F0 of the talker's voice. The processor also includes a tone generator to generate a tone based on the F0 of the talker's voice. The processor further includes pitch controls to ensure that the frequency of the tone remains in an audible frequency region for the listener. In some implementations, the processor modulates the talker's voice in frequency with the extracted fundamental frequency. In some implementations, the processor determines the amplitude envelope of the F0 of the talker's voice and modulates the F0 of the talker's voice in amplitude according to the amplitude envelope. In some implementations, the processor combines the modulation in frequency and the modulation in amplitude. The processor includes an amplifier to amplify the modulated signals and a delivery mechanism to deliver the amplified modulated signals to the cochlear implant. In some implementations, F0 and amplitude envelope cues are delivered to the user using frequency compression and transposition, In some implementations, the processor can be built into the cochlear implant. In other implementations, the processor can be operatively coupled to the implant. In some implementations, the device may be manufactured as a complementary component to another device, such as a CI. In this type of implementation, a single housing may contain both devices, in the interest of user comfort or to take advantage of shared resources.

In some implementations, the systems described in this specification, and the techniques that the described systems perform can be used for populations other than patients with CIs, for example, profoundly deafened individuals. Given the extremely limited acoustic hearing of such individuals, the F0 shift and variability controls will be particularly important in enhancing speech understanding.

What is claimed is:

1. A computer-implemented method to enhance speech understanding, the method comprising:
   receiving speech from a talker at a system including one or more computers, the speech including audio signals;
   extracting, at the system, a fundamental frequency from the audio signals, wherein the extracted fundamental frequency is unique to the talker;
   modulating, at the system, a tone in frequency with the extracted fundamental frequency of the received speech; and
   delivering the modulated tone as an acoustic signal.

2. The method of claim 1, further comprising:
   modulating, at the system, the tone in amplitude with an amplitude envelope of the received speech;
   providing the tone of the speech, modulated in frequency with the extracted fundamental frequency of the received speech, and in amplitude with the amplitude envelope of the received speech,
   wherein the modulated tone is amplified prior to the delivering.

3. The method of claim 2, wherein the amplitude envelope is obtained by half-wave rectification and low-pass filtering.

4. The method of claim 1, further comprising modulating the tone of the speech in frequency with dynamic changes of the extracted fundamental frequency.

5. The method of claim 4, wherein the dynamic changes of the extracted fundamental frequency are obtained using YIN algorithm.

6. A computer-readable medium tangibly encoding software instructions executable by one or more data processing apparatus to perform operations comprising:
   receiving speech from a talker, the speech including audio signals;
   extracting a fundamental frequency from the audio signals, wherein the extracted fundamental frequency is unique to the talker;
   modulating a tone in frequency with the extracted fundamental frequency of the received speech;
   amplifying the modulated tone; and
   delivering the modulated tone as an acoustic signal.

7. The computer-readable medium of claim 6, further comprising:
   modulating the tone of the speech in amplitude with an amplitude envelope of the received speech; and
   providing the tone, modulated in amplitude with the amplitude envelope of the received speech.

8. The computer-readable medium of claim 7, wherein the amplitude envelope is obtained by half-wave rectification and low-pass filtering.

9. The computer-readable medium of claim 6, further comprising modulating the tone of the speech in frequency with dynamic changes of the extracted fundamental frequency.

10. The computer readable medium of claim 9, wherein the dynamic changes of the extracted fundamental frequency are obtained using YIN algorithm.

11. A cochlear implant system comprising:
    a cochlear implant;
    means for receiving speech from a talker, the speech including audio signals;
    means for extracting a fundamental frequency from the audio signals, wherein the extracted fundamental frequency is unique to the talker;
    means for modulating a tone in frequency with the extracted fundamental frequency of the received speech; and
    means for providing the modulated tone to the cochlear implant as an acoustic signal.

12. The system of claim 11, further comprising means for:
    modulating the tone in amplitude with an amplitude envelope of the received speech; and
    providing the tone of the speech, modulated in amplitude with the amplitude envelope.

13. The system of claim 12, wherein the amplitude envelope is obtained by half-wave rectification and low-pass filtering of the received speech.

14. The system of claim 11, further comprising means for modulating the tone in frequency with dynamic changes to the extracted fundamental frequency.

15. The system of claim 14, wherein the dynamic changes of the extracted fundamental frequency are obtained using YIN algorithm.

16. A system comprising:
    a first transformer to receive audio signals and transform the received audio signals into a frequency-domain representation;
    a processor operatively coupled to the transformer, the processor including:
       a frequency compression unit to perform frequency compression of the frequency-domain representation of the audio signal,
       a frequency transposition unit operatively coupled to the frequency compression unit to perform frequency transposition of the frequency-domain representation of the audio signal on which the frequency compression has been performed;
    a second transformer operatively coupled to the processor to transform the compressed and transposed audio signals into a time-domain representation; and
    a transmitter operatively coupled to the second transformer to deliver the signals in the time-domain representation as acoustic signals.

17. The system of claim 16, further comprising an amplifier operatively coupled to the second transformer to amplify the signals in the time-domain representation.

18. The system of claim 17, further comprising a level control unit operatively coupled to the amplifier to control a level by which the amplifier amplifies the signals in the time-domain representation.

19. The system of claim 16, wherein the frequency compression is applied to the frequency region in which the fundamental frequency of most talkers occurs.

20. The system of claim 16, wherein the frequency transposition is applied such that the frequency region in which the fundamental frequency of most talkers occurs is audible to the user.

21. The system of claim 16, further comprising an audio transducing device to receive the signals in the time-domain representation delivered by the second transformer.

* * * * *